(12) United States Patent
Liu et al.

(10) Patent No.: US 9,445,955 B2
(45) Date of Patent: *Sep. 20, 2016

(54) ABSORBENT ARTICLE WITH A MULTIFUNCTIONAL SIDE PANEL

(71) Applicant: The Procter & Gamble Company, Cincinnati, OH (US)

(72) Inventors: Kaung-kai Liu, Cincinnati, OH (US); Joseph David Lussier, Milton, MA (US); Mary Elizabeth Davis, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 233 days.

This patent is subject to a terminal disclaimer.

(21) Appl. No.: 14/192,944

(22) Filed: Feb. 28, 2014

(65) Prior Publication Data

US 2014/0180236 A1    Jun. 26, 2014

Related U.S. Application Data

(63) Continuation of application No. 11/198,614, filed on Aug. 5, 2005, now Pat. No. 8,663,184.

(51) Int. Cl.
| | | |
|---|---|---|
| *A61F 13/15* | (2006.01) | |
| *A61F 13/20* | (2006.01) | |
| *A61F 13/56* | (2006.01) | |
| *A61F 13/496* | (2006.01) | |
| *A61F 13/514* | (2006.01) | |
| *A61F 13/84* | (2006.01) | |

(52) U.S. Cl.
CPC ......... *A61F 13/5655* (2013.01); *A61F 13/496* (2013.01); *A61F 13/4963* (2013.01); *A61F 13/51496* (2013.01); *A61F 13/565* (2013.01); *A61F 13/84* (2013.01); *A61F 2013/15243* (2013.01); *A61F 2013/15861* (2013.01)

(58) Field of Classification Search
CPC ............ A61F 13/496; A61F 13/4963; A61F 13/51496; A61F 13/5622; A61F 13/5655; A61F 13/84; A61F 2013/15243
USPC ................ 604/367, 385.24–385.25, 385.27, 604/385.3, 386–387
See application file for complete search history.

(56) References Cited

U.S. PATENT DOCUMENTS

| | | | |
|---|---|---|---|
| 2,075,189 | A | 3/1937 | Galligan et al. |
| 3,848,594 | A | 11/1974 | Buell |
| 3,860,003 | A | 1/1975 | Buell |
| 4,107,364 | A | 8/1978 | sisson |

(Continued)

FOREIGN PATENT DOCUMENTS

| | | |
|---|---|---|
| EP | 0 547 497 B1 | 3/1997 |
| EP | 0 937 446 A2 | 8/1999 |
| EP | 1 279 357 A1 | 1/2003 |
| EP | 1 287 799 A2 | 3/2003 |

(Continued)

*Primary Examiner* — Michele M Kidwell
(74) *Attorney, Agent, or Firm* — William E. Gallagher

(57) ABSTRACT

An absorbent article may comprise a chassis having a front waist region, a rear waist region, a crotch region between the front waist region and the rear waist region, a pair of longitudinal edges, and a pair of side panels extending between and connecting the front waist region and the rear waist region to form a leg opening. Each side panel may comprise a stretch laminate joined by a mechanical bond. The article may bear a chassis graphic disposed on a backsheet and a side panel graphic disposed on a side panel.

6 Claims, 12 Drawing Sheets

(56) References Cited

U.S. PATENT DOCUMENTS

| | | |
|---|---|---|
| 4,209,563 A | 6/1980 | Sisson |
| 4,463,045 A | 7/1984 | Ahr et al. |
| 4,515,595 A | 5/1985 | Kievit et al. |
| 4,610,678 A | 9/1986 | Weisman et al. |
| 4,662,875 A | 5/1987 | Hirotsu et al. |
| 4,663,220 A | 5/1987 | Wisneski et al. |
| 4,673,402 A | 6/1987 | Weisman et al. |
| 4,695,278 A | 9/1987 | Lawson |
| 4,699,622 A | 10/1987 | Toussant et al. |
| 4,710,189 A | 12/1987 | Lash |
| 4,720,415 A | 1/1988 | Vander Wielen et al. |
| 4,795,454 A | 1/1989 | Dragoo |
| 4,808,178 A | 2/1989 | Aziz et al. |
| 4,816,025 A | 3/1989 | Foreman |
| 4,834,735 A | 5/1989 | Alemany et al. |
| 4,834,741 A | 5/1989 | Sabee |
| 4,846,815 A | 7/1989 | Scripps |
| 4,888,231 A | 12/1989 | Angstadt |
| 4,892,536 A | 1/1990 | Desmarais et al. |
| 4,894,060 A | 1/1990 | Nestegard |
| 4,909,803 A | 3/1990 | Aziz et al. |
| 4,940,464 A | 7/1990 | Van Gompel et al. |
| 4,946,527 A | 8/1990 | Battrell |
| 4,963,140 A | 10/1990 | Robertson et al. |
| 4,965,122 A | 10/1990 | Morman |
| 4,981,747 A | 1/1991 | Morman |
| 4,990,147 A | 2/1991 | Freeland |
| 5,026,364 A | 6/1991 | Robertson |
| 5,037,416 A | 8/1991 | Allen et al. |
| 5,064,421 A | 11/1991 | Tracy |
| 5,092,861 A | 3/1992 | Nomura et al. |
| 5,114,781 A | 5/1992 | Morman |
| 5,116,662 A | 5/1992 | Morman |
| 5,137,537 A | 8/1992 | Herron et al. |
| 5,143,679 A | 9/1992 | Weber et al. |
| 5,147,345 A | 9/1992 | Young et al. |
| 5,151,092 A | 9/1992 | Buell et al. |
| 5,156,793 A | 10/1992 | Buell et al. |
| 5,167,897 A | 12/1992 | Weber et al. |
| 5,221,274 A | 6/1993 | Buell et al. |
| 5,224,405 A | 7/1993 | Pohjola |
| 5,226,992 A | 7/1993 | Morman |
| 5,246,433 A | 9/1993 | Hasse et al. |
| 5,260,345 A | 11/1993 | Desmarais et al. |
| 5,269,775 A | 12/1993 | Freeland et al. |
| 5,330,458 A | 7/1994 | Buell et al. |
| 5,336,545 A | 8/1994 | Morman |
| 5,342,338 A | 8/1994 | Roe |
| 5,359,525 A | 10/1994 | Weyenberg |
| 5,387,207 A | 2/1995 | Dyer et al. |
| 5,397,316 A | 3/1995 | Lavon et al. |
| 5,470,639 A | 11/1995 | Gessner et al. |
| 5,518,801 A | 5/1996 | Chappell et al. |
| 5,540,976 A | 7/1996 | Shawyer et al. |
| 5,554,143 A | 9/1996 | Roe et al. |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| 5,635,290 A | 6/1997 | Stopper et al. |
| 5,643,588 A | 7/1997 | Roe et al. |
| 5,659,538 A | 8/1997 | Stuebe et al. |
| 5,667,609 A | 9/1997 | Liu |
| 5,681,298 A | 10/1997 | Brunner et al. |
| 5,779,831 A | 7/1998 | Schmitz |
| 5,797,892 A | 8/1998 | Glaug et al. |
| 5,865,823 A | 2/1999 | Curro |
| 5,883,028 A | 3/1999 | Morman et al. |
| 5,897,545 A | 4/1999 | Kline et al. |
| 5,938,648 A | 8/1999 | Lavon et al. |
| 5,957,908 A | 9/1999 | Kline et al. |
| 5,980,087 A | 11/1999 | Brandon et al. |
| 5,997,989 A | 12/1999 | Gessner et al. |
| 6,001,460 A | 12/1999 | Morman et al. |
| 6,004,306 A | 12/1999 | Robles et al. |
| 6,015,764 A | 1/2000 | McCormack et al. |
| 6,045,543 A * | 4/2000 | Pozniak ............ A61F 13/5622 604/385.01 |
| 6,096,668 A | 8/2000 | Abuto et al. |
| 6,103,647 A | 8/2000 | Shultz et al. |
| 6,107,537 A | 8/2000 | Elder et al. |
| 6,120,487 A | 9/2000 | Ashton |
| 6,120,489 A | 9/2000 | Johnson et al. |
| 6,224,699 B1 | 5/2001 | Bett et al. |
| 6,225,243 B1 | 5/2001 | Austin |
| 6,253,159 B1 | 6/2001 | Bett et al. |
| 6,264,641 B1 | 7/2001 | Van Gompel et al. |
| 6,266,436 B1 | 7/2001 | Bett et al. |
| 6,313,372 B1 | 11/2001 | Suzuki |
| 6,352,528 B1 * | 3/2002 | Weber ............... A61F 13/5622 604/385.01 |
| 6,429,526 B1 | 8/2002 | Balock et al. |
| 6,432,098 B1 | 8/2002 | Kline et al. |
| 6,443,940 B1 | 9/2002 | Ashton et al. |
| 6,444,064 B1 | 9/2002 | Henry et al. |
| 6,448,467 B1 | 9/2002 | Herrlein et al. |
| 6,465,073 B1 | 10/2002 | Morman et al. |
| 6,478,786 B1 * | 11/2002 | Glaug ............... A61F 13/49011 604/385.27 |
| 6,479,154 B1 | 11/2002 | Walton et al. |
| 6,503,236 B1 | 1/2003 | Uitenbroek et al. |
| 6,579,274 B1 | 6/2003 | Morman et al. |
| 6,617,016 B2 | 9/2003 | Zhang et al. |
| 6,623,837 B2 | 9/2003 | Morman et al. |
| 6,627,564 B1 | 9/2003 | Morman et al. |
| 6,642,427 B2 | 11/2003 | Roe et al. |
| 6,680,265 B1 | 1/2004 | Smith et al. |
| 6,702,795 B2 | 3/2004 | Klemp |
| 6,719,742 B1 | 4/2004 | McCormack et al. |
| 6,733,483 B2 | 5/2004 | Raufman et al. |
| 6,743,314 B2 | 6/2004 | Henry et al. |
| 6,761,711 B1 | 7/2004 | Fletcher et al. |
| 6,766,817 B2 | 7/2004 | Da Silva |
| 6,811,865 B2 | 11/2004 | Morman et al. |
| 6,849,067 B2 | 2/2005 | Fletcher et al. |
| 6,849,324 B2 | 2/2005 | Meece et al. |
| 6,875,710 B2 | 4/2005 | Eaton et al. |
| 6,905,488 B2 | 6/2005 | Olson |
| 6,909,028 B1 | 6/2005 | Shawyer et al. |
| 6,918,404 B2 | 7/2005 | Da Silva |
| 6,942,894 B2 | 9/2005 | Alberg et al. |
| 6,955,733 B2 | 10/2005 | Miller et al. |
| 6,957,160 B2 | 10/2005 | Miller et al. |
| 6,960,834 B2 | 11/2005 | Nakamura et al. |
| 7,056,411 B2 | 6/2006 | Desai et al. |
| 7,066,586 B2 | 6/2006 | Da Silva |
| 7,123,981 B2 | 10/2006 | Dollevoet et al. |
| 7,169,137 B2 | 1/2007 | Shimada |
| 7,223,818 B2 | 5/2007 | Autran et al. |
| 7,285,255 B2 | 10/2007 | Kadlec et al. |
| 7,301,036 B2 | 11/2007 | Parmee et al. |
| 7,695,464 B2 | 4/2010 | Fletcher et al. |
| 2002/0111596 A1 | 8/2002 | fletcher et al. |
| 2002/0138062 A1 | 9/2002 | Kuen et al. |
| 2003/0028165 A1 | 2/2003 | Curro et al. |
| 2003/0065298 A1 | 4/2003 | Krishnaswamy et al. |
| 2003/0087059 A1 | 5/2003 | Jackson et al. |
| 2003/0088220 A1 | 5/2003 | Molander et al. |
| 2003/0091807 A1 | 5/2003 | Desai et al. |
| 2003/0120240 A1 | 6/2003 | Buell et al. |
| 2003/0162458 A1 | 8/2003 | Tsujiyama et al. |
| 2003/0167049 A1 | 9/2003 | Gibbs |
| 2004/0092902 A1 | 5/2004 | Hoffman et al. |
| 2004/0110442 A1 | 6/2004 | Rhim et al. |
| 2004/0127876 A1 | 7/2004 | Stevens |
| 2004/0132374 A1 | 7/2004 | Kobayashi |
| 2004/0193133 A1 | 9/2004 | Desai et al. |
| 2005/0027274 A1 | 2/2005 | Suzuki et al. |
| 2005/0096618 A1 | 5/2005 | Magee et al. |
| 2005/0106980 A1 | 5/2005 | Abed et al. |

(56) References Cited

U.S. PATENT DOCUMENTS

| | | |
|---|---|---|
| 2005/0124952 A1 | 6/2005 | Zehner et al. |
| 2005/0214461 A1 | 9/2005 | Desai et al. |
| 2005/0222546 A1 | 10/2005 | Vargo et al. |
| 2006/0025737 A1 | 2/2006 | Song et al. |
| 2006/0212010 A1 | 9/2006 | Roe et al. |
| 2006/0212018 A1 | 9/2006 | Roe et al. |
| 2006/0247594 A1 | 11/2006 | Nickel et al. |
| 2007/0032766 A1 | 2/2007 | Liu et al. |
| 2007/0073261 A1 | 3/2007 | Ashton et al. |
| 2007/0287982 A1 | 12/2007 | Lodge et al. |
| 2007/0287983 A1 | 12/2007 | Lodge et al. |

FOREIGN PATENT DOCUMENTS

| | | |
|---|---|---|
| JP | 09-300504 A | 11/1997 |
| WO | WO 95-16746 A1 | 6/1995 |
| WO | WO 00/37006 A1 | 3/2001 |
| WO | WO 02-091968 A2 | 11/2002 |
| WO | WO 2005-041834 A1 | 5/2005 |
| WO | WO 2005-102239 A1 | 11/2005 |
| WO | WO 2006-017518 A2 | 2/2006 |
| WO | WO 2006-017674 A1 | 2/2006 |
| WO | WO 2006-028911 A1 | 3/2006 |
| WO | 2006-127519 A2 | 11/2006 |
| WO | 2007-017817 A3 | 7/2007 |

\* cited by examiner

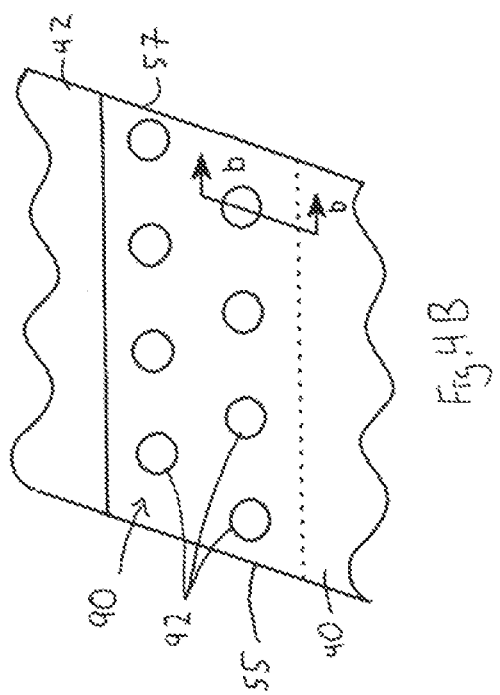
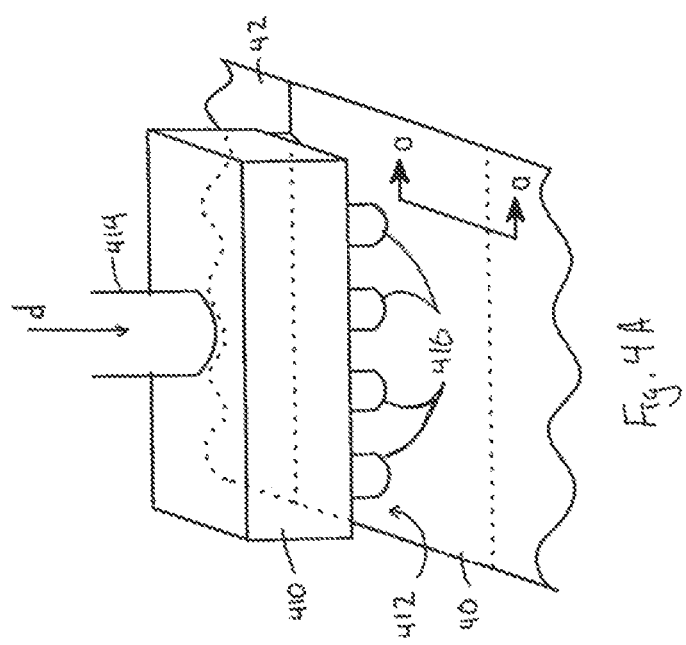

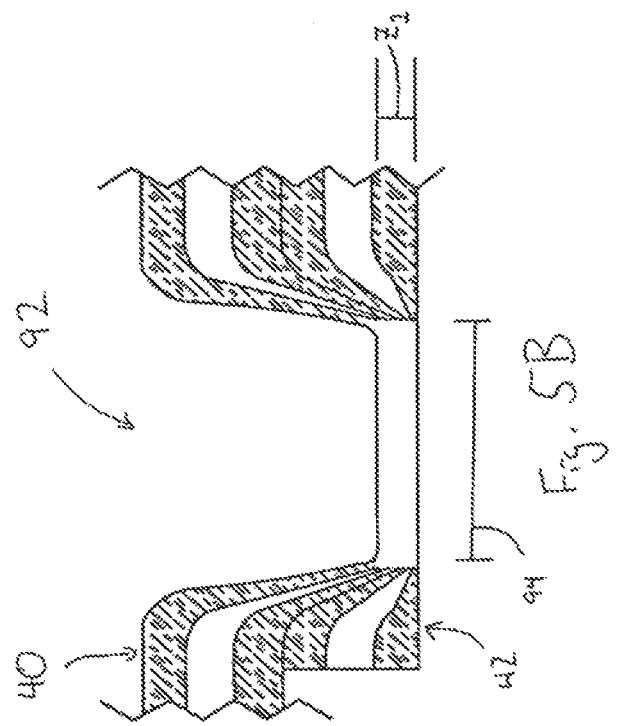
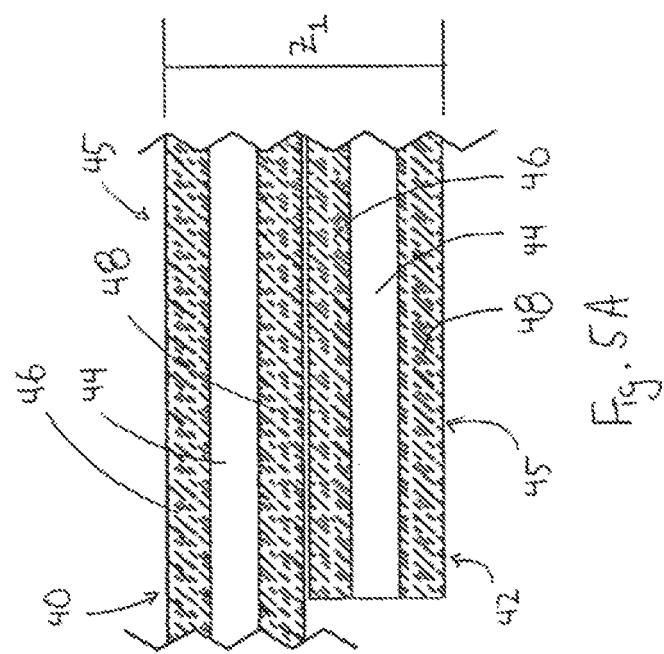

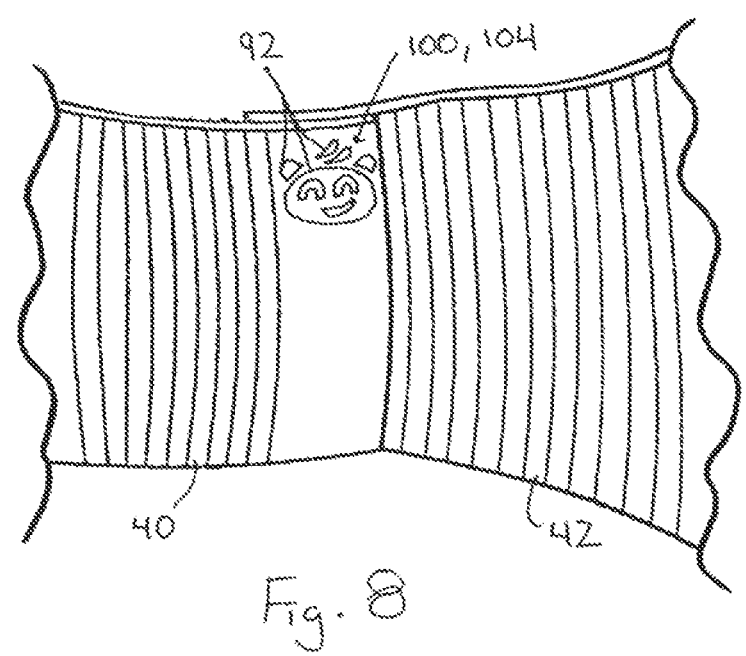

ABSORBENT ARTICLE WITH A MULTIFUNCTIONAL SIDE PANEL

FIELD OF INVENTION

This invention relates to elastic side panel laminates exhibiting improved color homogeneity and informational indicia for use on absorbent articles such as diapers.

BACKGROUND OF THE INVENTION

Absorbent articles such as disposable diapers, pull-on diapers, training pants, sanitary napkins, pantiliners, incontinence briefs, and the like, are well known in the art and are highly effective for absorbing and containing urine and other bodily exudates. Since their introduction into the marketplace, absorbent articles have continued to improve with regard to fit and functionality. Absorbent articles are constructed to provide a snug and comfortable fit around the waist and legs of a wearer while maintaining the ability to contain large quantities of exudates without leakage or adverse impact to the wearer's skin.

However, absorbent articles such as diapers have not advanced quite as significantly in regard to overall design. For many years, diapers were predominately white with no color, graphics, printing, or the like. Recent diaper designs have introduced both color and graphics to diapers. Many commercially available diapers now exhibit multi-color graphics oh the outer-facing surface of chassis. The outer-facing surface (i.e., diaper surface in proximity to garments while the diaper is being worn) is commonly a laminate of a polymeric film which provides some degree of liquid impermeability and a nonwoven cover which provides an improved cloth-like feel to the diaper. Diapers have been produced with multi-color graphics disposed on the polymeric film. These graphics are visible through the nonwoven outer cover which exhibits some degree of translucence. Diapers have also been produced. where the multi-color graphics are disposed on the nonwoven outer cover. However, the nonwoven generally must be of a sufficient basis weight if deeply saturated colors are desired.

Color consistency and graphic integrity are more easily controlled when printing to the outer-facing surface of the chassis because the chassis or at least a large portion of the chassis exhibits minimal elasticity. As a result of having little or no elasticity, the colors and graphics on the chassis do not experience the deforming effects of elastic extension and retraction.

Color and graphics have only recently been introduced to highly extensible regions of absorbent articles such as elastic side panels. Side panels are typically constructed from a stretch laminate having at least one elastic inner layer and typically two nonwoven layers with the elastic inner layer disposed in between. One common way of achieving a colored side panel is by coloring the nonwoven. This is typically done by adding pigment, dye, or other colorant to the fiber or filaments before formation of the nonwoven. Alternatively, a nonwoven web may be printed upon utilizing common print techniques such as gravure printing, inkjet printing, and the like. However, the nonwoven webs typically used in absorbent articles and, particularly, in side panels are of a relatively low basis weight. Since nonwoven are commonly formed by random lay-down of the constituent fibers or filaments, the resulting nonwoven web may be non-uniform with areas of high fiber or filament concentration and areas of low fiber or filament concentration. Regardless of coloration techniques (e.g., printing, impregnation, coating, etc.), the nonwoven may exhibit a mottled appearance. Areas of high fiber/filament concentration may appear more saturated than areas of low fiber/filament concentration. This mottled appearance is undesirable since it communicates low quality to consumers. The basis weight of the nonwoven can be increased to compensate for the mottled appearance, but this comes at additional cost without providing a proportional functional benefit (i.e., improved softness, barrier protection, abrasion resistance, etc).

Furthermore, the resulting stretch laminate may exhibit undesirable properties given the formation process for the laminate. For example, a stretch laminate may be formed by stretch bonding. In stretch bonding, an elastic member (such as elastic strands, bands, ribbons, films, or the like) are joined to a substrate (such as a nonwoven) while the elastic member is in a stretched configuration. The substrate is typically in a relaxed, unstretched configuration When the elastic member is joined thereto. Generally, the elastic member may be stretched to at least 25% of its relaxed length. However, when used as side panels, the elastic members may be stretched well in excess of 100% of the member's relaxed length. After joining, the elastic member is allowed to relax thereby gathering the substrate and creating a stretch laminate. The gathered substrate typically exhibits rugocities (i.e., wrinkles). When the nonwoven is colored, the rugocities can cause the nonwoven to appear mottled with varying light and dark hued areas. Again, a mottled appearance is undesirable.

Another deficiency present in absorbent articles is the lack of visual cues to aid in application of the product. This is particularly true with pant-type diapers which are often intended for use by children as they transition from wearing conventional diapers to underwear. However, young children and babies, especially once they begin walking, commonly wear pant-type diapers, which are typically easier for a user to apply and remove in a standing position and, therefore, emulate underwear. Pant-type diapers are applied by threading the wearer's legs through leg holes in the article, pulling the article aver the wearer's hips and buttocks, and correcting or adjusting the fit of the article once it is in position.

It is desirable for pant-type diapers to facilitate the overall dressing learning process by making it easier for the child to successfully apply the product. Due to physiological, psychological, or other factors, most children, particularly in the 12-30 month age range, are naturally inclined to grab the most easily visible and accessible portion of the pant-type diapers, which is the front waist region. Because the pant-type diapers must be pulled over the buttocks and hips, the tendency to pull at the front of the product often leads to failure and frustration because this action increases the circumferential tension in the back of the diaper, causing it to lodge tightly at the bottom of the buttocks. Further, no vertical tension is applied to the area that could dislodge the product, which is the back waist region of the article. Accordingly, it is more advantageous for the child to grasp and pull the product from the sides, thereby distributing vertical pulling force to both the front and back regions.

Accordingly, it would be desirable to provide an absorbent article having stretch laminate exhibit a more uniform color. It is also desirable that the stretch laminate not exhibit mottled coloration that is present in existing colored stretch laminates. It is further desirable to provide an absorbent article providing visual cues to the user or wearer.

SUMMARY OF THE INVENTION

The present invention is directed to an absorbent article having a multifunctional elastic side panel. One such absorbent article may comprise a chassis having a front waist region, a rear waist region, a crotch region between the front waist region and the rear waist region, a pair of longitudinal edges, and a pair of side panels extending between and connecting the front waist region and the rear waist region to form a leg opening, wherein each side panel has a waist edge, a leg edge, and distal edge. Each side panel may comprise a uniformly colored stretch laminate. The stretch laminate may comprise a colored elastomeric member and a first substrate joined to the elastomeric material.

Another suitable absorbent article may comprise a chassis having a front waist region, a rear waist region, a crotch region between the front waist region and the rear waist region, and a pair of longitudinal edges. The chassis may comprise a topsheet, a backsheet, and an absorbent core disposed between said topsheet and backsheet. The article may also comprise a front side panel extending laterally from the longitudinal edge of the chassis in the front waist region and a rear side panel extending laterally from the longitudinal edge of the chassis in the rear waist region. A mechanical bond may join the front side panel and the rear side panel to form a waist opening and a pair of leg openings. The mechanical bond forms an informational indicia.

Another suitable absorbent article comprises a chassis having a front waist region, a rear waist region, a crotch region between the front waist region and the rear waist region, and a pair of longitudinal edges. The chassis comprises a liquid permeable topsheet, a backsheet, and an absorbent core disposed between the topsheet and backstreet. The article further comprises a front side panel extending laterally from the longitudinal edge of the chassis in the front waist region and a rear side panel extending laterally from the longitudinal edge of the chassis in the rear waist region. The front and rear side panels each have a proximal edge. The article further comprises a mechanical bond joining the proximal edge of the front side panel or the rear side panel to respective front waist region or rear waist region. The mechanical bond forms informational indicia.

BRIEF DESCRIPTION OF THE DRAWINGS

While the specification concludes with claims pointing out and distinctly claiming the present invention, it is believed the same will be better understood by the following drawings taken in conjunction with the accompanying specification wherein like components are given the same reference number.

FIG. 4A-B are schematic illustrations of a suitable pressure bonding apparatus, process, and resulting bonded side panels.

FIG. 5A is a cross-sectional view of the side panels of FIG. 4A taken along sectional line a-a.

FIG. 5B is a cross-sectional view of the joined side panels of FIG. 4B taken along sectional line b-b.

FIG. 8 is enlarged views of a suitable embodiment of a bond forming an informational indicia comprising a character graphic.

DETAILED DESCRIPTION OF THE INVENTION

Figure 1:
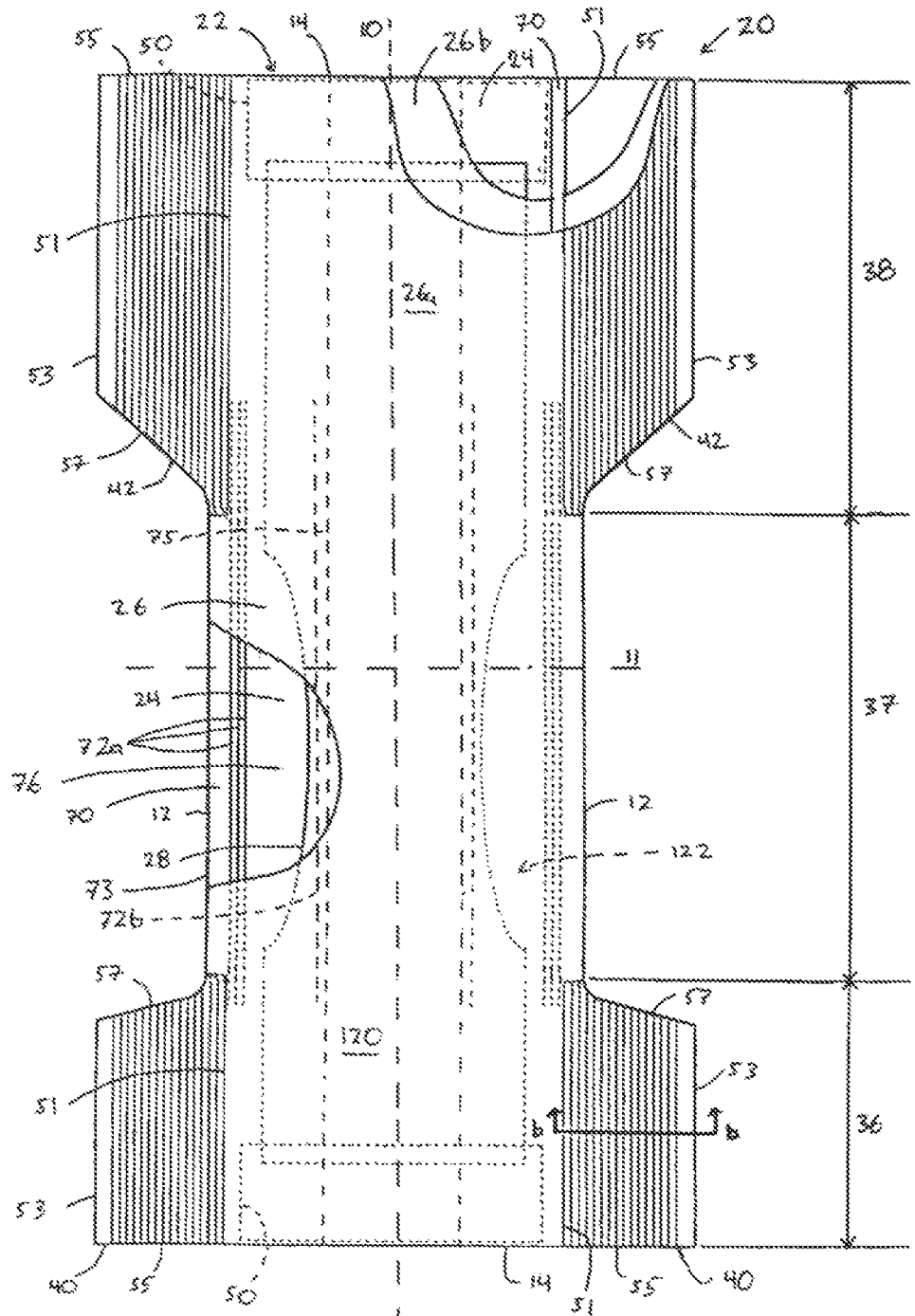
FIG. 1 is a plan view of an exemplary disposable absorbent article in a flat, uncontracted, unseamed state.

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Mechanical bond" is a non-adhesive attachment technique for joining two or more elements, components, regions, or webs. Suitable mechanical bonds include heat bonds, pressure bonds, ultrasonic bonds, dynamic mechanical bonds, or any other suitable non-adhesive attachment means or combinations of these attachment means as are known in the art.

"Proximal" and "Distal" refer respectively to the location of an element relatively near to or far from the longitudinal or lateral centerline of a structure (e.g., the proximal edge of a longitudinally extending element is located nearer to the longitudinal centerline than the distal edge of the same element is located relative to the same longitudinal centerline).

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Longitudinal" refers to a direction running substantially perpendicular from a waist edge to an opposing waist edge of the article and generally parallel to the maximum linear dimension of the article. Directions within 45 degrees of the longitudinal direction are considered to be "longitudinal"

"Lateral" refers to a direction running from a longitudinal edge to an opposing longitudinal edge of the article and generally at a right angle to the longitudinal direction. Directions within 45 degrees of the lateral direction are considered to be "lateral."

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid, water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable." As is well known in the art, a common method for measuring the permeability to water, urine, or synthetic urine of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

"Extendibility" and "extensible" mean that the width or length of the component in a relaxed state can be extended or increased.

"Elastic," "elastomer," and "elastomeric" refer to a material which generally is able to extend to a strain of at least 50% without breaking or rupturing, and is able to recover substantially to its original dimensions after the deforming force has been removed.

"Elastomeric material" is a material exhibiting elastic properties.

"Outboard" and "inboard" refer respectively to the location of an element disposed relatively far from or near to the longitudinal centerline of the diaper with respect to a second element. For example, if element A is outboard of element B, then element A is farther from the longitudinal centerline than is element B.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

The present invention relates to an absorbent article having a uniformly colored stretch laminate and/or informational indicia. FIG. 1 shows an exemplary disposable absorbent article in the form of a pant. The pant 20 is shown in a plan view in a flat, uncontracted state (i.e., without elastic induced contraction) with side panels 40, 42 in an unseamed configuration. Cut-away sections are provided to show underlying detail. The garment-facing surface 120 of the pant 20 is facing the viewer. The pant has an opposing body-facing surface 122. The pant 20 includes a longitudinal centerline 10 and a lateral centerline 11. The pant 20 may comprise a chassis 22. The pant 20 and chassis 22 are shown to have a front waist region 36, a rear waist region 38 opposed to the front waist region 36, and a crotch region 37 located between the front waist region 36 and the rear waist region 38. The waist regions 36 and 38 generally comprise those portions of the pant 20 which, when worn, encircle the waist of the wearer. The waist regions 36 and 38 may include elastic elements such that they gather about the waist of the wearer to provide improved fit and containment. The crotch region 37 is that portion of the pant 20 which, when the pant 20 is worn, is generally positioned between the legs of the wearer.

The outer periphery of chassis 22 is defined by longitudinal edges 12 and lateral edges 14. The longitudinal edges 12 may be oriented generally parallel to the longitudinal centerline 10. However, for better fit, longitudinal edges 12 may be curved or angled to produce, for example, an "hourglass" shape diaper when viewed in a plan view. The lateral edges 14 may be oriented generally parallel to the lateral centerline 11.

The chassis 22 may comprises a liquid permeable topsheet 24, a backsheet 26, and an absorbent core 28 between the topsheet 24 and the backsheet 26. The absorbent core 28 may have a body-facing surface and a garment facing-surface. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In certain embodiments, the chassis 22 comprises the main structure of the pant 20 with other features may added to form the composite diaper structure. While the topsheet 24, the backsheet 26, and the absorbent core 28 may be assembled in a variety of well-known configurations, preferred diaper configurations are described generally in U.S. Pat. Nos. 3,860,003; 5,151,092; 5,221,274; 5,554,145; 5,569,234; 5,580,411; and 6,004,306.

The topsheet 24 is generally a portion of the pant 20 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers e.g., polyester or polypropylene fibers), or a combination of natural and synthetic fibers. The topsheet 24 is generally supple, soft feeling, and non-irritating to a wearers skin. Generally, at least a portion of the topsheet 24 is liquid pervious, permitting liquid to readily penetrate through the thickness of the topsheet 24. A suitable topsheet 24 is available from BBA Fiberweb, Brentwood, Tenn. as supplier code 055SLPV09U. Any portion of the topsheet 24 may be coated with a lotion as is known in the art. Examples of suitable lotions include those described in U.S. Pat. Nos. 5,607,760; 5,609,587; 5,635,191; and 5,643,588. The topsheet 24 may be fully or partially elasticized or may be foreshortened so as to provide a void space between the topsheet 21 and the core 28. Exemplary structures including elasticized or foreshortened topsheets are described in more detail in U.S. Pat. Nos. 4,892,536, 4,990, 147; 5,037,116; and 5,269,775.

The absorbent core 28 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222.

The backsheet 26 is generally positioned such that it may be at least a portion of the garment-facing surface 120 of the pant 20. Backsheet 26 may be designed to prevent the exudates absorbed by and contained within the pant 20 from soiling articles that may contact the pant 20, such as bed sheets and undergarments. In certain embodiments, the backsheet 26 is substantially water-impermeable. Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the pant 20 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer, as illustrated in the cut-away of FIG. 1. The backsheet 26 may comprise an outer cover 26a and an inner layer 26b. The outer cover 26a may be made of a soft, non-woven material. The inner layer 26b may be made of a substantially water-impermeable film. The outer cover 26a and an inner layer 26b may be joined together by adhesive or any other suitable material or method. A suitable outer cover 26a is a nonwoven available from Corovin GmbH, Peine, Germany as supplier code A18AH0, and a suitable inner layer 26b is a polymeric film available from RKW Gronau GmbH, Gronau, Germany as supplier code PGBR4WPR.

The pant 20 may include one or more pairs of leg cuffs. Leg cuffs may also be known as barrier cuffs, gasketing cuffs, outer leg cuffs, leg bands, side flaps, elastic cuffs, second cuffs, inner leg cuffs or "stand-up" elasticized flaps. Furthermore, a multiple cuffs may be provided by way of a dual cuff. FIG. 1 shows a suitable dual cuff 70. The dual cuff 70 may have a proximal edge 75 and a distal edge 73. In some embodiments, such as the open shown in FIG. 1, the distal edge 73 of the cuff 70 may be coterminous with the longitudinal edge 12. The cuff 70 may comprise a cuff substrate 76. The cuff substrate 76 may be constructed from woven webs, nonwoven webs, polymeric films, laminates thereof, and the like. In certain embodiments, the cuff substrate 76 may be a spunbond web, a meltblown web, or combinations thereof (e.g., S/M, S/M/S, S/M/M/S, etc.). In certain embodiments, the cuff substrate 76 may comprise a portion of the topsheet 24, backsheet 26 (including the outer cover 26a and/or inner layer 26b), or any other suitable substrate used in the formation of the pant 20. The cuff substrate 76 may be treated to increase its hydrophobicity. Suitable hydrophobic treatments include, but are not limited to, the application of hydrophobic surface coating (as exemplified in U.S. patent application Ser. No. 11/055,743, entitled "Hydrophobic Surface Coated Absorbent Articles And Associated Methods", filed on Feb. 10, 2005) and flouro-treatment as exemplified in co-pending U.S. Patent Application Publication No. 2004/0092902A1).

The cuff 70 may further comprise one or more elastic members 72 (such as elastic strands) or sets of elastic members 72 joined to the cuff substrate 76. The cuff substrate 76 may encircle, envelope, or otherwise wrap the elastic members 72 so as to prevent direct contact of the elastic member 72 to a wearer's skin. In some embodiments, the elastic members 72 may be disposed between the cuff substrate 76 and some other material, layer, or substrate of the pant 20 such as the topsheet 24, outer cover 26a, and/or inner layer 26b. In FIG. 1, the cuff 70 comprises a set of elastic member 72a in proximity to the distal edge 73 and an elastic member 72b is proximity to the proximate edge 75. The cuff 70 may be joined to the chassis 22 by any bonding technique known in the art including adhesive and mechanical bonding. Further description of diapers having suitable leg cuff construction may be found in U.S. Pat. Nos. 5,667,609, 4,808,178, 4,909,803, 4,695,278, 4,795,454, and 3,860,003.

The diaper 20 may also comprise an elastic waist feature 50. The elastic waist feature 50 is generally intended to elastically expand and contract to dynamically fit the wearer's waist. The waist feature 50 may enable the diaper 20 to provide improved fit and containment. The diaper may have two elastic waist features 50, one positioned in the first waist region 36 and one positioned in the second waist region 38. The elastic waist feature 50 may be joined to the body-facing surface 122 of the diaper 20. The elastic waist feature 50 may be joined to the topsheet 24. The elastic waist feature 50 may be constructed in a number of different configurations including those described in U.S. Pat. Nos. 4,515,595; 4,710,189; 5,151,092; and 5,221,274. Other suitable waist configurations may include waistcap features such as those described in U.S. Pat. Nos. 5,026,364 and 4,816,025

The pant 20 may include front side panels 40 and rear side panel 42. Each side panel 40, 42 may have a proximal edge 51 and distal edge 53. The proximal edge 51 generally is the edge adjacent to the chassis 22. Each side panel may also have a waist edge 55 and a leg edge 57. The front side panels 40 may be disposed laterally outboard of the longitudinal edge 12 of the chassis 22 within the front waist region 36. The rear side panels 42 may be disposed laterally outboard of the longitudinal edge 12 of the chassis 22 within the rear waist region 38.

Figure 2A:
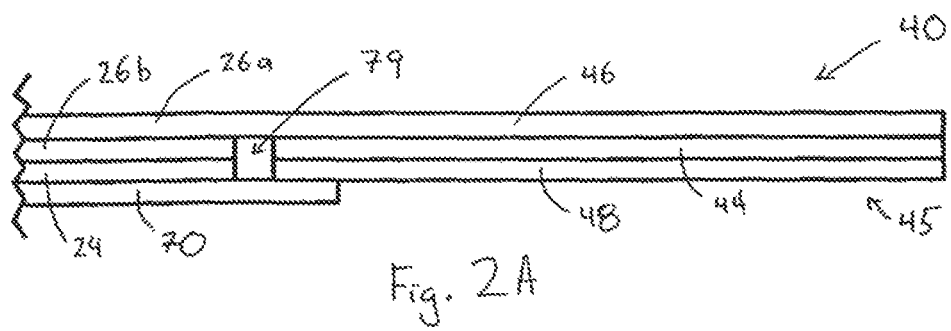
FIG. 2A is a cross-sectional of the article of FIG. 1 taken through sectional line b-b showing one embodiment of a suitable side panel construction.

FIG. 2A is a cross-sectional view of the pant 20 taken along section line b-b of FIG. 1 showing suitable embodiments for side panel 40, 42 construction. While the cross-section is of the front side panel 40, the rear side panel 42 may be constructed in a similar manner. The front and rear side panels 40, 42 may be constructed of a uniformly colored stretch laminate 45. The uniformly colored stretch laminate 45 may comprise at least one colored elastic member 44 joined to at least a first substrate 46. In other suitable embodiments, the uniformly colored stretch laminate 45 may comprise at least one color bearing elastic member 44 disposed between a first substrate 46 and a second substrate 48. In other embodiments, the stretch laminate 45 may comprise multiple elastic members and/or substrates wherein at least one elastic member is colored.

FIG. 2A illustrates the front side panel 40 as a unitary element of the pant 20. In this embodiment, the side panel 40 is not a separate element secured to the pant 20, but rather is formed from and/or is an extension of at least one or possibly several of the various layers of the chassis 22. As shown in FIG. 2A, the front side panel 40 shares a common layer (e.g., outer cover 26*a*) with the front side panel 40. The common layer (e.g., outer cover 26*a*) may also serve as the first substrate 46 for the stretch laminate 45. In this embodiment, the stretch laminate 45 is shown with the optional second substrate 48 disposed such that the elastic member 44 is between the first substrate 46 and the second substrate 48. The side panel 40 may be joined to one or more of the layers, webs, and/or substrates of the chassis such as the topsheet 24, the backsheet 26 (including the outer cover 26*a* and/or inner layer 26*b*), the cuff 70, and the like. In FIG. 2A, the side panel 40 is joined to the cuff 70. The side panel 40 may be disposed such that a gap 79 exists between the elastic member 44 and the inner layer 26*b* and/or the topsheet 24. The gap 79 may have a lateral width of some non-zero dimension.

Figure 2B:
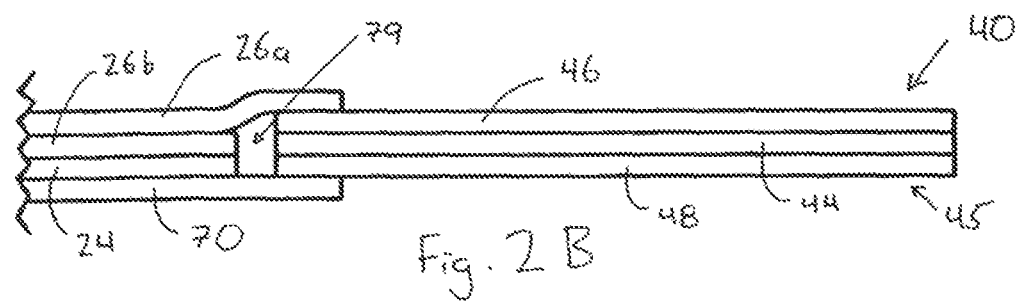
FIG. 2B is a cross-sectional view showing one embodiment of a suitable side panel construction.

In other embodiments, the front side panels 40 may be a discrete element that is joined to the chassis 22, as shown in FIG. 2B. Discrete side panels typically do not share a common, continuous layer or substrate with the chassis 22. However, it should be noted that some degree of overlap may be necessary in order to bond the side panel 40 to the chassis 22, but such overlapping regions of the chassis 22 and side panel 40, 42 are minimal. The side panel 40 comprises a uniformly colored stretch laminate 45. The uniformly colored stretch laminate 45 is formed of the elastic member 44 disposed between the first substrate 46 and the optional second substrate 48. The side panel 40 may be joined to one or more of the layers, webs, and/or substrates of the chassis such as the topsheet 24, the backsheet 26 (including the outer cover 26*a* and/or inner layer 26*b*), the cuff 70, and the like. In FIG. 2B, the side panel 40 is joined, to the cuff 70 and the outer cover 26*a*. The side panel 40 may be disposed such that a gap 79 exists between the elastic member 44 and both the inner layer 26*b* and/or the topsheet 24. The gap 79 may have a lateral width of some non-zero dimension.

The side panels 40, 42 may be joined to the chassis 22 by any bonding method known in the art such as adhesive bonding, pressure bonding, heat bonding, and the like. A suitable elastic back ear 42 may be a laminate comprising an elastomeric film (such as is available from Tredegar Corp, Richmond, Va., as supplier code X25007) disposed between two nonwoven layers (such as is available from BBA Fiberweb, Brentwood, Tenn. as supplier code FPN332).

The elastic member 44 may be provided in a variety of well known forms including, but are not limited to films, apertured films, bands, strands, individualized fibers, scrims, cross-hatch arrays, foams, or combinations thereof. In particularly suitable embodiments, the elastic member 44 may be a planar member in the form of a film, apertured film, scrim, foam, or other sheet-like structures where the length and width of the member are many orders of magnitude larger than the thickness. It is believed that these forms provide a more uniform coloration to the stretch laminate 45. The elastic member 44 may comprise an elastomeric polymer, either alone or in combination. Suitable elastomeric polymers include, but are not limited to, homopolymers (e.g., crosslinked poly(isoprene)), block copolymers, random copolymers, alternating copolymers, and graft copolymers. Suitable elastomeric polymers include styrenic block copolymers (e.g., styrene/isoprene/styrene, styrene/butadiene/styrene, styrene/ethylene-butylene/styrene), natural and synthetic rubbers, polyisoprene, neoprene, polyurethanes, silicone rubbers, hydrocarbon elastomers, ionomers, ethylene copolymers (e.g., ethylene vinyl acetates, ethylene/propylene copolymers, ethylene/propylene/diene terpolymers) and the like. Compounding and formation (e.g., extrusion, molding, casting, etc.) of elastic members comprising elastomeric polymers may be done by any conventional means within the art.

The elastic member 44 may be colored by a variety of suitable coloration techniques. The elastic member 44 may be colored, by way of printing, coating, and impregnating. Various printing methods may be used to impart color including, but not limited to, letterpress, flexography, gravure, offset lithography, screen, and inkjet. Suitable coating techniques are well-known in the art and include, but are not limited to, bead extruders, slot die coaters, spray nozzles, dip tanks, brushes, and combinations thereof Color may be imparted to the elastic member by way of impregnation of a colorant into subsistent materials. For example, if the elastic member comprises an elastomeric polymer, an appropriate colorant such as a dye, pigment, or combinations thereof may be compounded into the polymer. For example, the colorant may be added to molten batch of polymer during film, fiber, or filament formation.

The uniformly colored stretch laminate 45 may comprise at least a first substrate 46 and, optionally, a second substrate 48. Suitable substrates 46, 48 include nonwoven webs, woven webs, knitted fabrics, films, film laminates, apertured films, nonwoven laminates, sponges, foams, scrims, and any combinations thereof. Suitable substrates 46, 48 may comprise natural materials, synthetic materials, or any combination thereof. For use in absorbent articles and particularly in pants, substrates 46, 48 are generally compliant, soft-feeling, and non-irritating to a wearer's skin. In certain embodiments, substrates 46, 48 may include nonwoven webs such as spunbond webs, meltblown webs, carded webs, and combinations thereof spunbond-meltblown composites and variants). In suitable embodiments, the substrate 46 allows the color of the underlying elastic member to be visually perceived. For example, in certain embodiments, substrates 46, 48 may be substantially transparent or substantially translucent. In the case of a substrate 46, 48 formed of a nonwoven web, the web may be substantially translucent by formation from translucent or transparent fibers or filaments. Furthermore, a nonwoven web may be constructed of a relatively low basis weight such that, even if the constituent fibers and/or filaments are substantially opaque, the resulting web is translucent. Optionally, the substrate 46, 48 may be colored by any technique suitable in the art.

The uniformly colored stretch laminate 45 and its components (i.e., elastic member 44 and substrate(s) 46, 48) may be of any suitable size or shape. In suitable embodiments, the uniformly colored stretch laminate 45 is substantially the same size and shape as the side panel 40, 42 of which it is a component. In certain embodiments, the colored elastic member 44 is sized such that it is coterminous with the leg edge 57 and waist edge 55 of the side panel 40, 42 of which it is a component. In certain other embodiments, the colored elastic member 44 is sized such that it is coterminous with the leg edge 57, waist edge 55, and proximal edge 51 of the side panel 40 42 of which it is a component. In other embodiments, the colored elastic member 44 is coterminous with the side panel 40, 42 of which it is a component.

The elastic member 44 and substrates 46, 48 may be joined by any bonding technique known in the art such as by adhesive bonds, heat bonds, pressure bonds, ultrasonic bonds, mechanical bonds, or combinations thereof.

The substrates 46, 48 may be elastic or inelastic. In certain embodiments, the substrates 46, 48 may exhibit little elasticity and may exhibit a relatively large modulus. The high modulus of the substrate 46, 48 may inhibit elongation of the resulting laminate of the substrate 46, 48 and elastic member 44. Several techniques are known in the art for addressing the problem of substrates 46, 48 that are extensible but not necessarily elastomeric.

One technique for creating a stretch laminate, which is commonly known as "stretch bonding," involves an elastic member such as elastic strands, bands, ribbons, films, or the like being joined to a substrate While the elastic member is in a stretched configuration. Generally, the elastic member may be stretched to at least 25% of its relaxed length. After joining, the elastic member is allowed to relax thereby gathering the substrate and creating a stretch laminate.

Another technique for creating a stretch laminate, which is commonly known as "neck bonding," involves an elastic member being bonded to a substrate while the substrate is extended and necked. In certain embodiments, the substrate may be a non-elastic substrate. Examples of neck-bonded laminates are described, in U.S. Pat. Nos. 5,226,992; 1,981, 747; 4,965,122; and 5,336,545. A variant of "neck bonding" is "neck stretch bonding," Neck stretch bonding refers to an elastic member being bonded to a substrate while the substrate is extended and necked and the elastic member is extended. Examples of necked stretch bonded laminates are described in U.S. Pat. Nos. 5,114,781 and 5,116,662.

In another technique for forming a stretch laminate, elastic members can be attached to a substrate in either a relaxed configuration or partially stretched configuration. The resulting laminate can be made stretchable (or more stretchable in the case of partially stretched strands or film) by subjecting the laminate to an elongation process which elongates the substrate permanently, but elongates the elastic members only temporarily. Such processes are known in the art as "zero strain" stretch laminate formation, and the elongation of such laminates may be accomplished with suitable means such as rollers, engaging teeth, or the like. Examples of zero strain activation processing and the resulting zero strain stretch laminates are described in U.S. Pat. Nos. 5,167,897 and 5,156,793. A suitable side panel 40, 42 may include a stretch laminate comprising an elastomeric film (such as is available from Tredegar Corp, Richmond, Va., as supplier code X25007) disposed between two nonwoven layers (such as is available from BBA Fiberweb, Brentwood, Tenn. as supplier code FPN332). As used herein, "zero strain stretch laminates" are stretch laminates formed by zero strain method as described herein.

Figure 3:
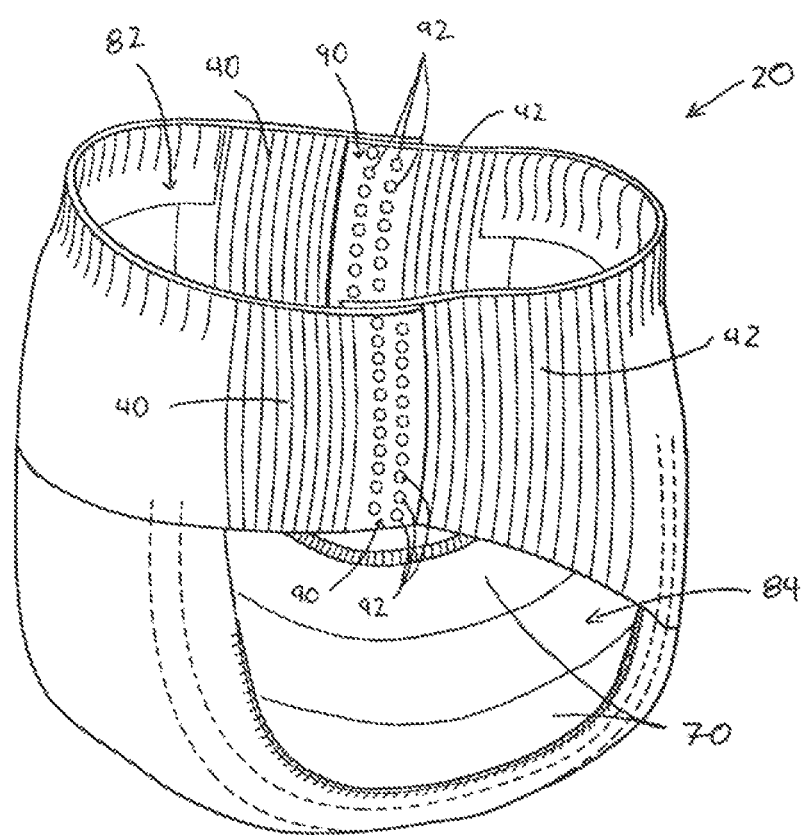
FIG. 3 is a perspective view of the article of FIG. 1 in a seamed configuration ready for wear.

FIG. 3 shows the pant 20 of FIG. 1 in a closed-state, ready for wear with the front side panel 40 and the rear side panel 42 joined so as to form a waist opening 82 and a pair of leg openings 84. To don the pant, a wearer need only insert his/her legs into the waist opening 82 and through the leg openings 84 and then raise the pant 20 up his/her legs until it is positioned around the lower torso. The front side panel 40 and the rear side panel 42 may be joined at a seam 90. Seams 90 are the areas where the adjacent front side panel 40 and rear side panel 42 may be permanently or refastenably joined. Permanently joined side panels 40, 42 are sufficiently joined to maintain connection prior to and during use of the pant. Permanently joined side panels may be frangible to facilitate removal and/or disposal. In certain embodiments, the seam 90 may comprise one or more mechanical bonds 92. FIG. 3 depicts the seam 90 comprising a plurality of mechanical bonds 92.

A variety of mechanical bonding techniques are known in the art. One such technique is pressure bonding. Pressure involves applying high pressure to compress and join the front side panel 40 and the rear side panel 42. FIG. 4A-B are schematic illustrations of a suitable pressure bonding apparatus and process. Portions of the front side panel 40 and the rear side panel 42 are shown in a partially overlapping configuration. A die head 410 with an engaging surface 412 is attached to a reciprocating member 414 The engaging surface 412 of the die head 410 may include one or more protrusions 416 from the otherwise relatively planar surface. The die head 410 and the protrusions 416 from the engaging surface 412 can be of any suitable size, shape, and/or pattern. The die head 410 may be configured with one or more protrusions 416 which may provide an informational indicia as described below. As shown in FIG. 4A, an array of cylindrical-shaped protrusions 416 are disposed on the engaging surface 412. With the side panels 40, 42 positioned underneath the die head, the reciprocating member 414 drives the die head 410 in direction d. The protrusions 416 contact and compress the side panels 40, 42. While not shown, typically the side panels 40, 42 may be backed by a steel plate or other like member to facilitate compression. The pressure applied to the side panels 40, 42 may result in localized heating of portions of the side panels 40, 42 adjacent to and underneath of the protrusions 416. The heat generated may result in temperatures that exceed the relatively low melting or softening points for the materials (such as polymeric materials) within the side panels 40, 42. The materials comprising the side panels 40, 42 may flow together at the site of the bond 92. The resulting bonded side panels 40, 42 are shown in FIG. 4B. Upon cooling, the materials may be fused together and/or may fuse together around the perimeter of the bond 92. A plurality of bonds 92 are typically created and may be arranged in a pattern that forms the seam 90 joining the front side panel 40 to the rear side panel 42. The seam 90 may span the longitudinal length of the front side panel 40 and rear side panel 42. The seam 90 may extend laterally from the leg edge 57 of the side panels 40, 42 to the waist edge 55 of the side panels 40, 42.

While mechanical bonds may join the side panels 40, 42, the bond 92 also impacts the physical characteristics of the side panels 40, 42. The bonds 92 may impart a discernable feature to the front side panels 40 and/or the rear side panel 42. Discernable features are any perceptible differences between the bond and areas surrounding and/or adjacent to the bond. Discernable features include differences in caliper, relative smoothness or roughness, color saturation, reflectivity, or other visual effect.

FIGS. 5A-B are comparisons of the side panels 40, 42 before and after bonding by the bonding apparatus shown in FIG. 4A. FIG. 5A is a partial cross-sectional view taken along sectional line a-a of FIG. 4A showing the side panels 40, 42 before mechanical bonding. The front side panel 40 may be made from a stretch laminate 45 comprising a colored elastic member 44 disposed between a first substrate 46 and a second substrate 48. The rear side panel 42 may have a like construction. The front and rear side panels 40, 42 have a combined, caliper of $z_1$. After being mechanically bonded, as shown in FIG. 5B, the side panels 40, 42 may be joined by the bond 92. As a result of the heat and pressure, the bond creates a bond zone 94 where some of the constituent layers of the front and rear side panels 40, 42 may meld together. In suitable embodiments, there should be some melding of at least one constituent layer from the front side panel 40 and at least one constituent layer from the rear side panel 42. The bond, zone 94 may have a caliper of $z_2$. Generally, the caliper of the size panels 40, 42 in regions adjacent to the bond zone 94 may remain approximately equal to the combined caliper $z_1$. One of the physical characteristics impacted by the mechanical bonding is localized caliper. Typically, the bond zone 94 caliper may be less than the combined caliper ($z_2 < z_1$).

certain embodiments, the bond zone 94 caliper may be 75% or less of the combined caliper (($z_2/z_1$)×100=0.75). In other embodiments, the bond zone 94 caliper may be 50% or less of the combined caliper. In other embodiments, the bond zone 94 caliper may be 25% or less of the combined caliper.

Another physical characteristic that may be modified by the mechanical bond 92 is the hand or softness of the side panels 40, 42. Prior to bonding, the outer most garment-facing layer of side panels 40, 42 may be the first substrate 46. Suitable substrates may be chosen that are low cost and have soft feel such as nonwovens including carded web or spunbond webs. The individual fibers and/or filaments of the nonwoven give the side panels 40, 42 loft and a luxurious, fabric-like feel. The bond 92 compresses the fibers and/or filaments such that the bond zone 94 has greater density than areas of the side panels 40, 42 adjacent to the bond zone 94. By increasing the density of the bond zone 94, the fabric-like nonwoven within this zone 94 may be compressed in a film-like structure. As a consequence, a visual and tactile difference results between the bond zones 94 and the areas surrounding the bond zone 94 which exhibit loft and a fabric-like feel.

Another physical characteristic that results from the mechanical bond 92 is saturation of the color within the bond zone 94. As mentioned in certain embodiments above, the side panels 40, 42 may be made from uniformly colored stretch laminate 45 which can comprise at least one colored elastic member 44 joined to at least one substrate 46. As previously mentioned, the mechanical bond compresses side panels 40, 42 within the bond zone 94 including the colored elastic member 44. The amount of colorant in the bond zone 94 is unchanged after the bonding occurs; however, since the side panels 40, 42 have been compressed within the bond zone 94, the concentration of the colorant may increase. The increased concentration may result in the bond zone 94 appearing to have a more saturated color than the areas surrounding the bond zone 94. It is further believed that the increased saturation may result from decreased light scattering caused by the substrate 46. The substrate 46 may, as a result its construction, diffuse or scatter light. For example, a nonwoven substrate placed over a colored elastic member 45 generally will reduce the perceived saturation of the colored elastic member 45. Since mechanical bond 92 may reduce the loft and fibrous composition of the nonwoven within the bond zone 94, the nonwoven may lose some of its diffusion property. Qualitatively, this may result in the bond zone 94 appearing more saturated in color compared to the areas surrounding the bond zone 94.

The bonds 92 may be configured to provide informational indicia, informational indicia are any graphic, symbol, icon, word, or other marking formed by one or more bonds 92 which exhibit a discernable feature wherein the indicia communicates a message, instruction, or idea to a user or elicits a cognitive response from a user. The informational indicia may rely on the user's prior experiences or knowledge to arrive at the desired message. The indicia may be targeted for older wearers or caregivers such as a parent. The indicia may be targeted to young wearers. In certain embodiments, the informational indicia depict simple concepts that may be understood at a basic or visceral level with no or little prior knowledge or experience by the user. It is the discernable feature created by the bond 92 which forms the informational indicia allowing the indicia to be at least visually perceived. While the following disclosure and figures describe certain embodiments, the embodiments are exemplary and not meant to limit the present invention. Numerous equivalents and variations to the informational indicia are within the scope of this disclosure.

Figure 6:
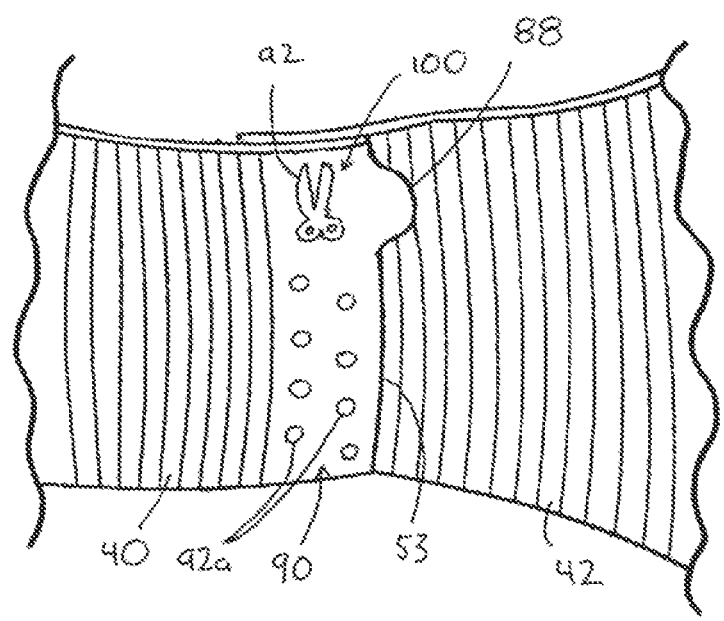
FIG. 6 is an enlarged view one suitable embodiment of a bond forming an informational indicia.

FIG. 6 depicts one suitable embodiment of a bond 92 which forms an informational indicia 100. The informational indicia 100 may be disposed on the seam 90 bonding the front side panel 40 and the rear side panel 42. In this embodiment, the informational indicia 100 may be in the form of a pair of scissors (as shown in FIG. 6) or some other graphic that communicates tearing or cutting. The bond 92 forming the informational indicia 100 may be permanent in that it maintains connection of the side panels 40, 42 prior to and during use of the pant. However, the bond 92 may be frangible to facilitate removal and/or disposal of the pant. The informational indicia 100 may communicate to the user the location where the separation of the bonds 92 may begin for removal of the product. Optionally, the informational indicia may be positioned in proximity to tear open tab 88, as shown in FIG. 6. The tab 88 is an extension of the side panel or one or more of the constituent layers of the side panel beyond an otherwise substantially linear edge (e.g., distal edge 53 as shown in FIG. 6, leg edge 57, or waist edge 55) of the side panel. The tear open tab 88 is designed to be a grip point for a user during the tearing or fracturing of the bonds. As shown in FIG. 6, the seam 90 may have one or more secondary mechanical bonds 92a that may or may not serve as informational indicia, but do serve to further join the side panels 40, 42.

Figure 7A:
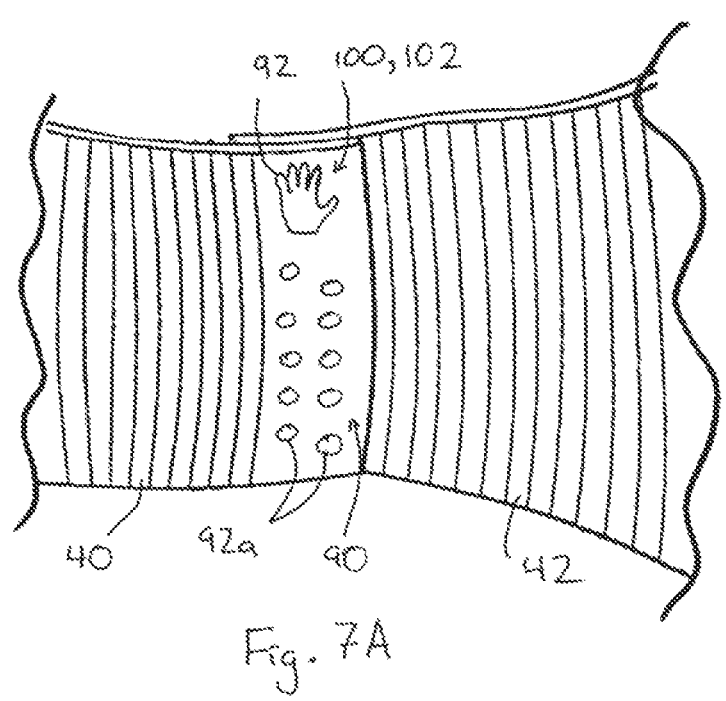
FIG. 7A-B are enlarged views of suitable embodiments of a bond forming an informational indicia comprising a hand graphic.
Figure 7B:
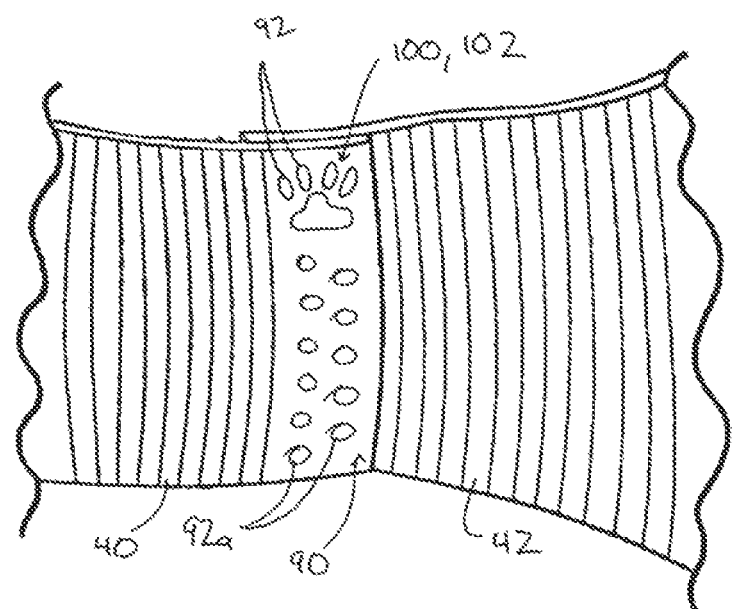
Figure 7C:
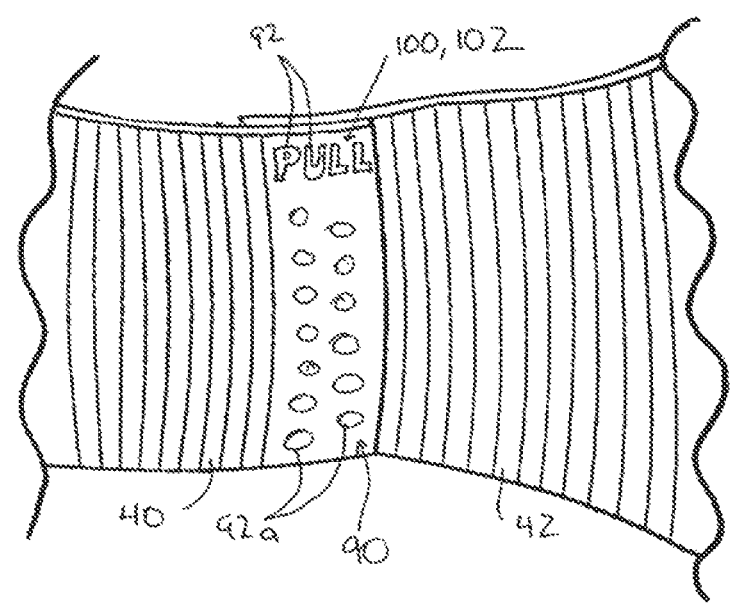
FIG. 7C is an enlarged view one suitable embodiment of a bond forming an informational indicia.

FIGS. 7A-C depict several suitable information indicia 100 formed from the bonds 92 joining the front side panel 40 to the rear side panel 42. The indicia 100 in each 31) figure may communicate where hands should be placed when donning or doffing the pant. Young users in particular tend to grasp the pant at locations that are not mechanically efficient for conveying the application force. For example, young users often place both hands close together along the front of the pant. Such hand placement does not effectively distribute application forces to the rear of the pant. By providing the informational indicia 100 depicted in FIGS. 7A-C, it is believed that wearers or users will grasp the pant at opposing seams 90 thereby distributing application forces more evenly around the pant. FIGS. 7A-B are examples of hand graphics 102. A hand graphic 102 is an informational indicia 100 that resembles a hand, a hand with a portion of an arm, or one or more portions of a hand (e.g., one or more fingers, one or more finger tips, one or more finger prints, a palm, a thumb, and the like). The hand graphic 102 may resemble a human hand (as is shown in FIG. 7A); an animal hand, paw, hoof, claw, talon, or the like (as shown in FIG. 7B); a cartoon character hand, a mythical creature hand;

silhouette of any aforementioned hands; prints of any aforementioned hands; and variants thereof. The hand graphic 102 is not limited to four fingers and a thumb. FIG. 7C is another suitable information indicia 100 communicating appropriate hand placement. The word "PULL" or any other word may be used to convey hand placement. In each of these embodiments, the seam 90 may have one or more optional secondary mechanical bonds 92a that may or may not serve as informational indicia, but do serve to farther join the side panels 40, 42.

In other suitable embodiments, the informational indicia 100 formed from bonds 92 may be in the form of or may include a character graphic 104 as shown in FIG. 8. The term "character graphic" is used herein to refer to a graphic containing an anthropomorphic image which may ascribe human shape, form, characteristic, motivation, and/or behavior to inanimate objects, animals, natural phenomena, toys, cartoon characters, and the like. Character graphics 104 need not be of the complete character (e.g., the face or head alone may be depicted). Character graphics 104 may be associated with popular characters from media, advertising, or a particular culture. Generally, the character graphic 104 is one that the user and particularly children care about and may identify with. Character graphics 104 may elicit increased interest in the pant by the wearer. This may be particularly beneficial when used on a training pant designed for a child being toilet trained. Increased awareness of the training product may serve as a signal to the child that he/she has progressed from traditional taped diapers.

Figure 9:
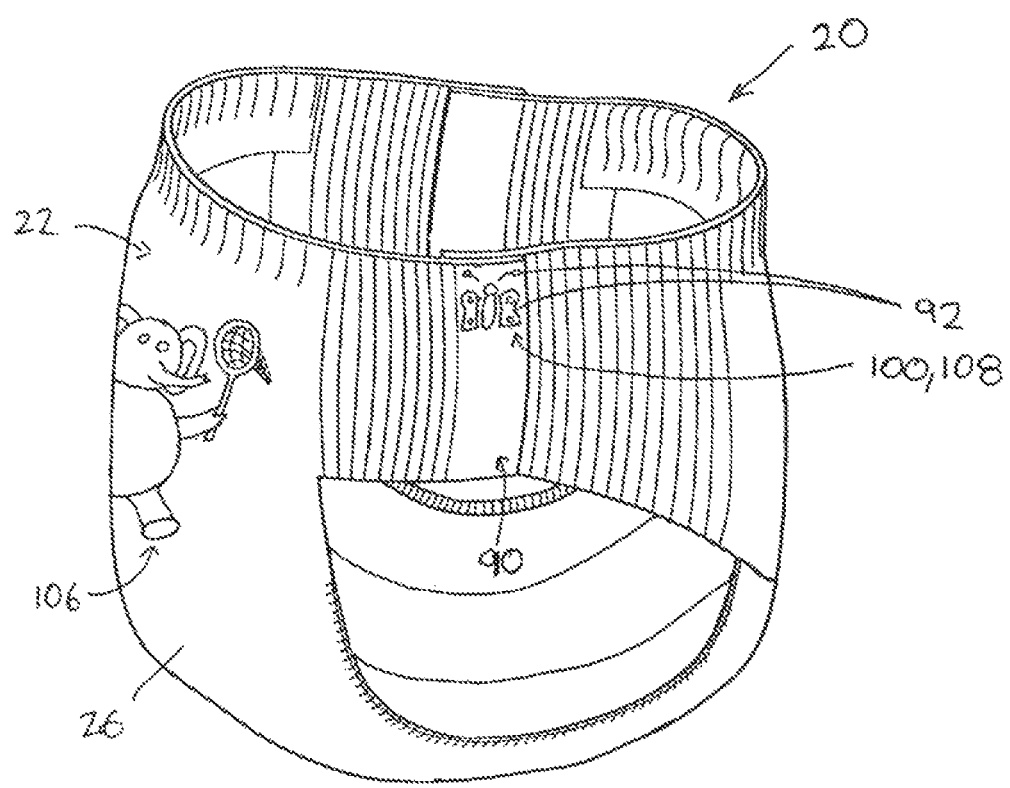
FIG. 9 is a perspective view of a disposable absorbent article comprising a chassis graphic and bond serving as an informational indicia comprising a relational graphic.

In other suitable embodiments as shown in FIG. 9, the pant 20 may include one or more chassis graphics 106. Chassis graphics 106 are any graphic, symbol, icon, word, or other marking that appears on the chassis 22 of the pant 20. The chassis graphic 106 may he disposed on the backsheet 26; however, graphics may be disposed on the interior (i.e., body-facing surface) of the pant or any substrates, layers, and/or elements of the pant. The chassis graphic 106 may be formed from a mechanical bond, printing, or any other suitable image formation technique.

In certain embodiments such as shown in FIG. 9, the bonds 92 may provide informational indicia 100 which may comprise a relational graphic 108. Relational graphics 108 are graphics that logically relate to, flow from, or connect with the chassis graphic 106, a character graphic 104, a hand graphic 102, or another informational indicia. Without wishing to be limited, suitable pairings of relational graphics to chassis graphics, character graphics, and/or hand graphics may include: the chassis graphic may include a character graphic holding or using a racquet, bat, glove, other sporting equipment or the like and the relational graphics may comprise balls, related sporting equipment or the like; the chassis graphic 106 may include a character graphic 104 holding a butterfly net or the like and the relational graphics 108 may comprise butterflies or the like (as shown in FIG. 6D); the chassis graphic include a character graphic holding flowers, plants, gardening tools or the like and the relational graphics may comprise flowers or plants; the chassis graphic may comprise an outer space scene or imagery and the relational graphics may comprise space ships, UFOs, comets, stars, planets, and the like; the chassis may be of specific environment such as a doll house, barn yard, school building or the like and the relational graphics may comprise dolls, animals, books, and the like which are specifically adapted to the environment; the chassis graphic may be a character graphic comprising a racecar and the object graphic comprising race flags; or other suitable relational graphics.

Figure 10:
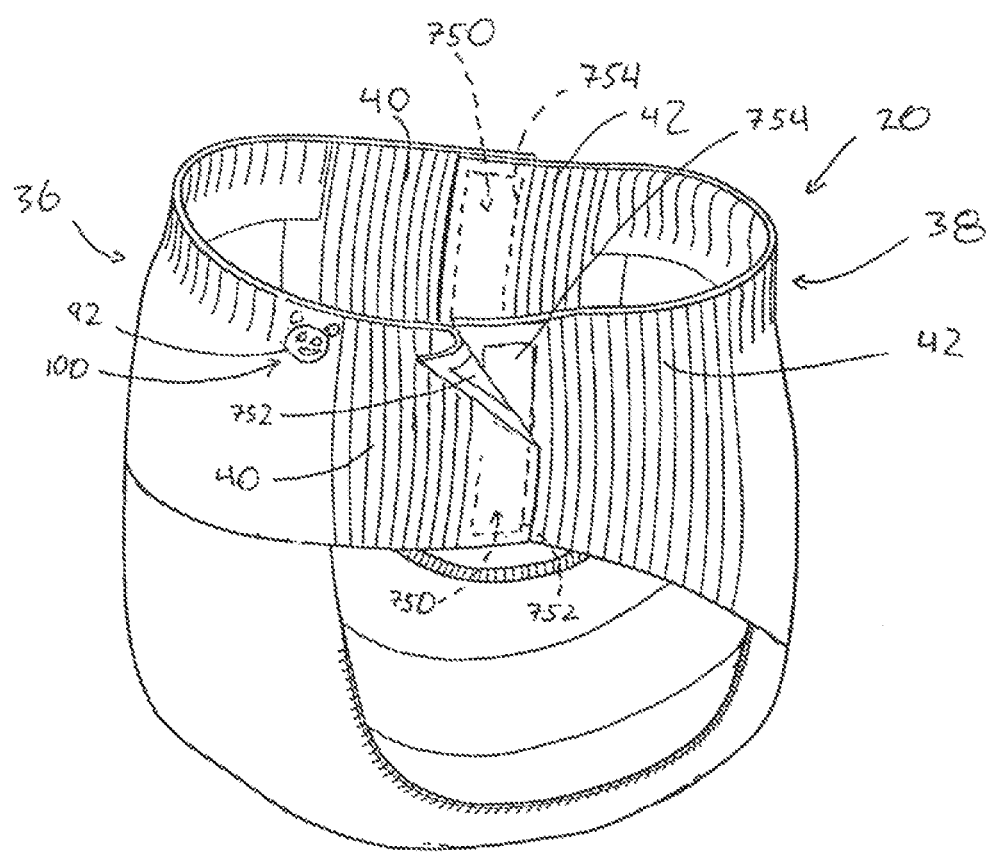
FIG. 10 is a perspective view of a disposable absorbent article comprising a fastening system and a bond forming an informational indicia.

While the above mechanical bonds 92 and resulting informational indicia 100 are disclosed as being utilized at a seam 90 to join a front side panel 40 and a rear side panel 42, mechanical bonds 90, and the resulting informational indicia 100, may be used to join other substrates, layers, and/or elements of the pant 20. For example, the front side panel 40 and rear side panels 42 may be joined to the respective waist regions 36, 38 of the pant 20 by using a mechanical bond 92 configured to provide the informational indicia 100. FIG. 10 depicts a pant 20 having a bond 92 joining the front side panel 40 to the front waist region 36 of the pant 20. The bond 92 may form the informational indicia 100. The pant 20 may also include a fastening system 750. When fastened, the fastening system 750 interconnects the front waist region 36 and the rear waist region 38 resulting in a waist circumference that may encircle the wearer during wear of the pant 20. The fastening system 750 may include an engaging member 752 and a receiving member 754. The engaging member 752 may comprise hooks, loops, an adhesive, a cohesive, or other fastening member. The receiving member 754 may comprise hooks, loops, an adhesive, a cohesive, or other fastening component that can receive the engaging member 752.

Suitable engaging member 752 and receiving member 754 combinations include but are not limited to hooks/loop, hooks/hooks, adhesive/polymeric film; cohesive/cohesive, adhesive/adhesive; tab/slot; and button/button hole. Exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 750 may also provide a means for holding the article in a disposal configuration as disclosed in U.S. Pat. No. 4,963,140. In certain embodiments, the pant 20 may be manufactured with the fastening system 750 in an engaged configuration (i.e., the engaging member 752 and the receiving member 754 are joined).

While the embodiments presented above are directed to a pant-type diaper, the uniformly colored stretch laminate and mechanical bonds configured to provide informational indicia may be disposed on other like absorbent articles such as taped diapers, adult incontinence products, feminine hygiene products, and the like.

All documents cited in the Detailed Description of the Invention are, in relevant part, incorporated herein by reference; the citation of any document is not to be construed as an admission that it is prior art with respect to the present invention. To the extent that any definition or meaning of a term in this written document conflicts with any definition or meaning of the term in a document incorporated by reference, the definition or meaning assigned to the term in this document shall govern.

While particular embodiments of the present invention have been illustrated and described, it would be obvious to those skilled in the art that various other changes and modifications can be made without departing from the spirit and scope of the invention. It should be apparent that combinations of such embodiments and features are possible and can result in executions within the scope of this invention. It is therefore intended to cover in the appended claims all such changes and modifications that are within the scope of this invention.

What is claimed is:

1. A disposable absorbent article comprising a pant, further comprising:
   a) a chassis comprising a longitudinal centerline, a front waist region, a rear waist region, a crotch region between the front waist region and the rear waist region, and a pair of longitudinal edges; wherein the chassis comprises a topsheet, backsheet, and an absorbent core disposed between the topsheet and backsheet;
   b) a side panel, comprising a front side panel portion extending laterally from the front waist region, and a rear side panel portion extending laterally from the rear waist region and attached to the front side panel portion;
   c) a mechanical bond disposed on the side panel and joining the front side panel portion and the rear side panel portion at a seam, the mechanical bond comprising a bond zone having a bond zone density that is greater than a density of material adjacent the bond zone, and a bond zone caliper that is less than a caliper of material adjacent the bond zone; and
   d) a chassis graphic disposed on the backsheet, and a side panel graphic disposed on the side panel.

2. The article of claim 1 wherein the side panel graphic is disposed in proximity to the seam.

3. The article of claim 1 Wherein the chassis graphic and the side panel graphic are relational graphics.

4. The article of claim 1 further comprising an intermediate graphic disposed laterally between the longitudinal centerline and the seam.

5. The article of claim 1 wherein the side panel comprises a stretch laminate comprising a first nonwoven web, a second nonwoven web and an elastic member sandwiched between the first and second nonwoven webs.

6. The article of claim 5 wherein the elastic member comprises elastic strands.

* * * * *